US012670646B2

(12) United States Patent (10) Patent No.: US 12,670,646 B2
Ketcha et al. (45) Date of Patent: Jun. 30, 2026

(54) METHOD AND APPARATUS FOR RECONSTRUCTING IMAGE ACQUISITIONS FOR EXTENDED FIELDS-OF-VIEW

(71) Applicant: Medtronic Navigation, Inc., Louisville, CO (US)

(72) Inventors: Michael D. Ketcha, Brookline, MA (US); Patrick A. Helm, Canton, MA (US)

(73) Assignee: Medtronic Navigation, Inc., Lafayette, CO (US)

( * ) Notice: Subject to any disclaimer, the term of this patent is extended or adjusted under 35 U.S.C. 154(b) by 117 days.

(21) Appl. No.: 18/608,624

(22) Filed: Mar. 18, 2024

(65) Prior Publication Data

US 2024/0346717 A1 Oct. 17, 2024

Related U.S. Application Data

(60) Provisional application No. 63/458,532, filed on Apr. 11, 2023.

(51) Int. Cl.
*G06T 12/20* (2026.01)
*A61B 6/00* (2024.01)
(52) U.S. Cl.
CPC ............ *G06T 12/20* (2026.01); *A61B 6/4447* (2013.01); *A61B 6/4476* (2013.01); *G06T 2210/22* (2013.01); *G06T 2211/421* (2013.01)
(58) Field of Classification Search
CPC ..... A61B 6/032; A61B 6/4435; A61B 6/4447; A61B 6/4476; A61B 6/5205;
(Continued)

(56) References Cited

U.S. PATENT DOCUMENTS 6,915,005 B1 * 7/2005 Ruchala .................. G06T 12/10
382/284
8,238,631 B2 8/2012 Hartmann et al.
(Continued)

FOREIGN PATENT DOCUMENTS

WO 2017214048 A1 12/2017

OTHER PUBLICATIONS

International Search Report and Written Opinion for related International Application No. PCT/IB2024/053497; date of mailing: Jul. 24, 2024; 10 pages.

*Primary Examiner* — David J Makiya
*Assistant Examiner* — Soorena Kefayati

(57) ABSTRACT

A method of reconstructing an extended FOV image of an imaging volume of a gantry of an X-ray imaging system includes: generating first projected and interpolated padding data for a first image of a central region of the imaging volume based on a first image of an annulus region of the imaging volume surrounding the central region; generating a first extended image of the central region based on the first projected and interpolated padding data; generating a second projected and interpolated padding data for the first image of the annulus region based on the first image of the central region; generating a first extended image of the annulus region based on the second projected and interpolated padding data; and performing back projection to reconstruct the extended field-of-view image based on the first and extended images of the central and annulus regions.

22 Claims, 11 Drawing Sheets

(58) Field of Classification Search
CPC ... A61B 6/5235; A61B 6/5241; G06T 11/005;
G06T 11/006; G06T 2210/22; G06T
2210/421
See application file for complete search history.

(56) References Cited

U.S. PATENT DOCUMENTS

| | | | | |
|---|---|---|---|---|
| 8,562,211 | B2* | 10/2013 | Helm | A61B 6/4452 378/197 |
| 9,757,077 | B2* | 9/2017 | Suzuki | A61B 6/5205 |
| 11,154,269 | B2* | 10/2021 | Shea | A61B 6/032 |
| 11,160,526 | B2* | 11/2021 | Yu | A61B 6/032 |
| 2005/0063507 | A1* | 3/2005 | Baba | A61B 6/466 378/11 |
| 2007/0025499 | A1* | 2/2007 | Bruder | A61B 6/032 378/9 |
| 2008/0089468 | A1* | 4/2008 | Heigl | G01N 23/046 378/20 |
| 2008/0267476 | A1* | 10/2008 | Langan | G06T 12/20 382/131 |
| 2010/0232565 | A1* | 9/2010 | Ye | A61B 6/032 378/19 |
| 2010/0290690 | A1* | 11/2010 | Hartmann | A61B 34/20 600/407 |
| 2011/0058647 | A1* | 3/2011 | Star-Lack | G16H 50/30 378/65 |
| 2011/0176717 | A1* | 7/2011 | Siren | A61B 6/4435 382/131 |
| 2011/0182400 | A1* | 7/2011 | Forthmann | A61B 6/032 378/22 |
| 2012/0099772 | A1* | 4/2012 | Helm | A61B 6/482 378/114 |
| 2012/0155736 | A1* | 6/2012 | Faul | A61B 6/032 382/131 |
| 2012/0177171 | A1* | 7/2012 | Gutfleisch | A61B 6/4085 378/62 |
| 2012/0250822 | A1* | 10/2012 | Helm | G01T 1/2018 378/62 |
| 2013/0077847 | A1* | 3/2013 | Hansis | G06T 12/20 382/131 |
| 2015/0117593 | A1* | 4/2015 | Ji | A61B 6/5205 378/19 |
| 2016/0166223 | A1* | 6/2016 | Besson | A61B 6/4007 378/9 |
| 2016/0210762 | A1* | 7/2016 | Fu | G06T 12/20 |
| 2016/0278719 | A1* | 9/2016 | Jensen | A61B 6/4441 |
| 2016/0324499 | A1* | 11/2016 | Sen Sharma | A61B 6/5258 |
| 2017/0042490 | A1* | 2/2017 | Takemoto | A61B 6/027 |
| 2020/0030634 | A1* | 1/2020 | Van Heteren | A61N 5/1067 |
| 2020/0121267 | A1* | 4/2020 | Deutschmann | A61B 6/4452 |
| 2020/0240934 | A1* | 7/2020 | Yi | G01N 23/046 |
| 2021/0007684 | A1* | 1/2021 | Mistretta | A61B 6/541 |

* cited by examiner

| | Key |
|---|---|
| ---------- | X-ray Beam to Capture Central Region |
| — · — · | X-ray Beam to Capture Annulus Region |

METHOD AND APPARATUS FOR RECONSTRUCTING IMAGE ACQUISITIONS FOR EXTENDED FIELDS-OF-VIEW

CROSS-REFERENCE TO RELATED APPLICATION

This application claims the benefit of and priority to U.S. Provisional Patent Application No. 63/458,532 filed Apr. 11, 2023, the entire disclosure of which is incorporated by reference herein.

FIELD

The present disclosure is directed to image reconstruction for a region of interest within an imaging system, and more particularly to image reconstruction for an extended field-of-view (FOV) of a volume within an imaging system.

BACKGROUND

This section provides background information related to the present disclosure which is not necessarily prior art.

A subject, such as a human patient, may undergo a surgical procedure to correct or augment an anatomy of the subject. The augmentation of the anatomy can include various procedures, such as movement or augmentation of bone, insertion of an implant (i.e., an implantable device), or other appropriate procedures. A surgeon can perform the procedure on the subject based on and/or with the assistance of images of the patient acquired by an imaging system. Some example imaging systems are magnetic resonance imaging (MRI) system, computed tomography (CT) system, and a fluoroscopy system (e.g., C-Arm or O-Arm® imaging systems).

Images of a patient can assist a surgeon in planning and performing a procedure. For example, images can assist a surgeon in performing a procedure with a less invasive technique by allowing the surgeon to view the anatomy of the patient without removing overlying tissue (including dermal and muscular tissue) during the procedure.

SUMMARY

This section provides a general summary of the disclosure, and is not a comprehensive disclosure of its full scope or all of its features.

A method of reconstructing an extended field-of-view image of an imaging volume of a gantry of an X-ray imaging system is disclosed. The method includes: performing a first spin of the gantry to capture a first set of images of a central region of the imaging volume; and performing a second spin of the gantry to capture a second set of images of an annulus region of the imaging volume surrounding the central region. The method further includes: generating first projected and interpolated padding data for a first image of the central region based on a first image of the annulus region, where the first set of images comprising the first image of the central region, and where the second set of images comprising the first image of the annulus region; generating a first extended image of the central region based on the first projected and interpolated padding data; generating a second projected and interpolated padding data for the first image of the annulus region based on the first image of the central region; generating a first extended image of the annulus region based on the second projected and interpolated padding data; and performing back projection to reconstruct the extended field-of-view image of the imaging volume based on the first extended image of the central region and the first extended image of the annulus region.

In another aspect of the disclosure, an imaging system is disclosed and includes a gantry and a processor. The gantry includes an aperture having an imaging volume in which a subject is disposed. The gantry includes an X-ray source and a detector array arranged to rotate about an isocenter of the gantry. The processor is configured to: spin the gantry a first time to capture via the detector array a first set of images of a central region of an imaging volume; and spin the gantry a second time to capture via the detector array a second set of images of an annulus region of the imaging volume surrounding the central region. The processor is further configured to: generate first projected and interpolated padding data for a first image of the central region based on a first image of the annulus region, the first set of images comprising the first image of the central region, and the second set of images comprising the first image of the annulus region; generating a first extended image of the central region based on the first projected and interpolated padding data; generating a second projected and interpolated padding data for the first image of the annulus region based on the first image of the central region; generating a first extended image of the annulus region based on the second projected and interpolated padding data; and performing back projection to reconstruct an extended field-of-view image of the imaging volume based on the first extended image of the central region and the first extended image of the annulus region.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

A field-of-view (FOV) of an internal volume within an imaging system may be imaged. This image can include an image of a subject located within the imaging volume. The subject may be a living subject, such as a human patient. Image data of a central region and an annulus region of the FOV may be acquired and combined to provide an image of the imaging volume that is greater than that of a single scan acquired by the imaging system. It is understood, however, that image data may be acquired of a non-living subject, such an inanimate subject including a housing, casing, interior of a super structure, or the like. For example, image data may be acquired of an airframe for various purposes, such as diagnosing issues and/or planning repair work.

An imaging system that is configured for orientating (or tilting) an X-ray source and a detector array and for the repositioning of the detector array relative to the X-ray source can be configured in different imaging geometries. The imaging system can be configured to increase a FOV for three-dimensional (3D) cone-beam-computed tomography (CBCT) imaging. The FOV can be increased beyond that provided when performing a single 360° scan including a single spin of the gantry including a 360° rotation of the x-ray source and detector array about the isocenter of the imaging system.

Figure 3:
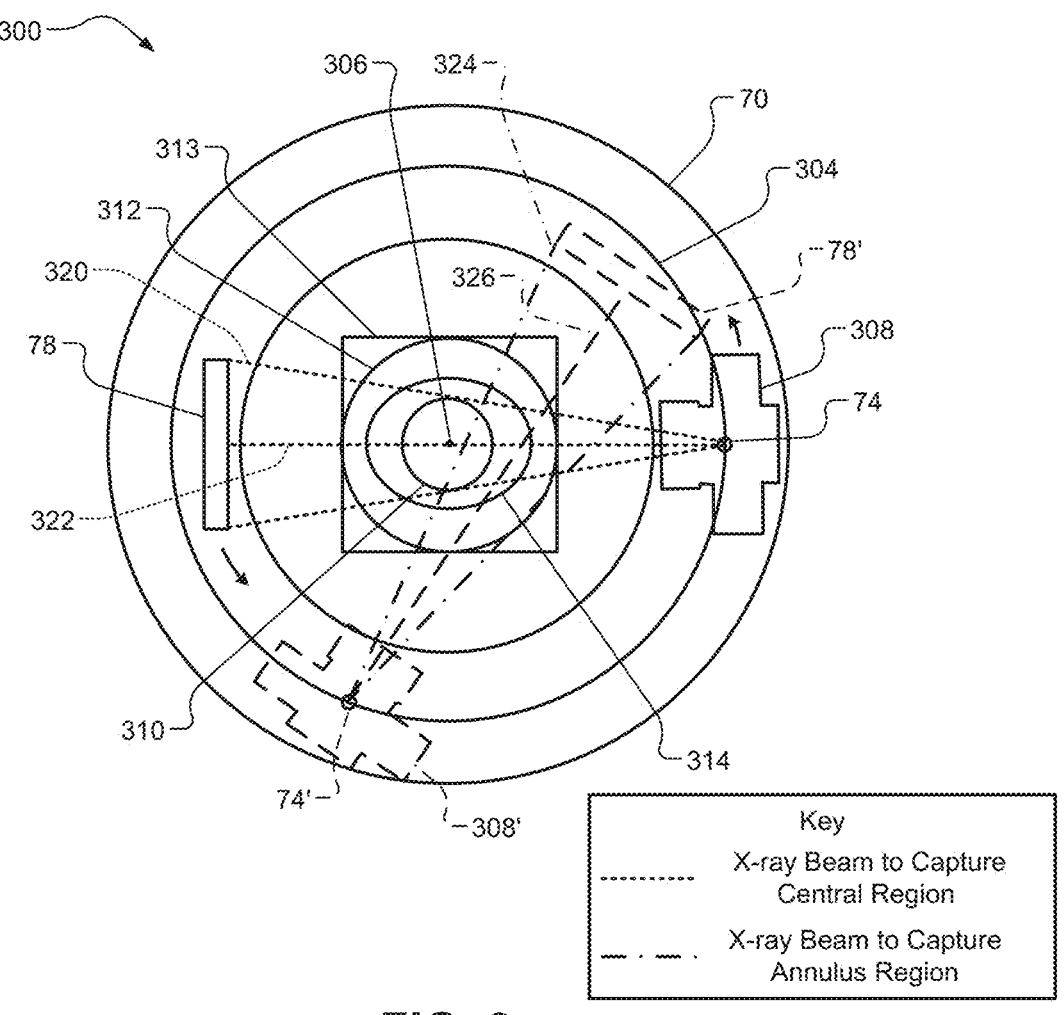
FIG. 3 is a cross-sectional side view of a portion of the imaging system of FIG. 1 illustrating source and detector orientations and positioning for central region and annulus scans in accordance with the present disclosure.
Figure 4:
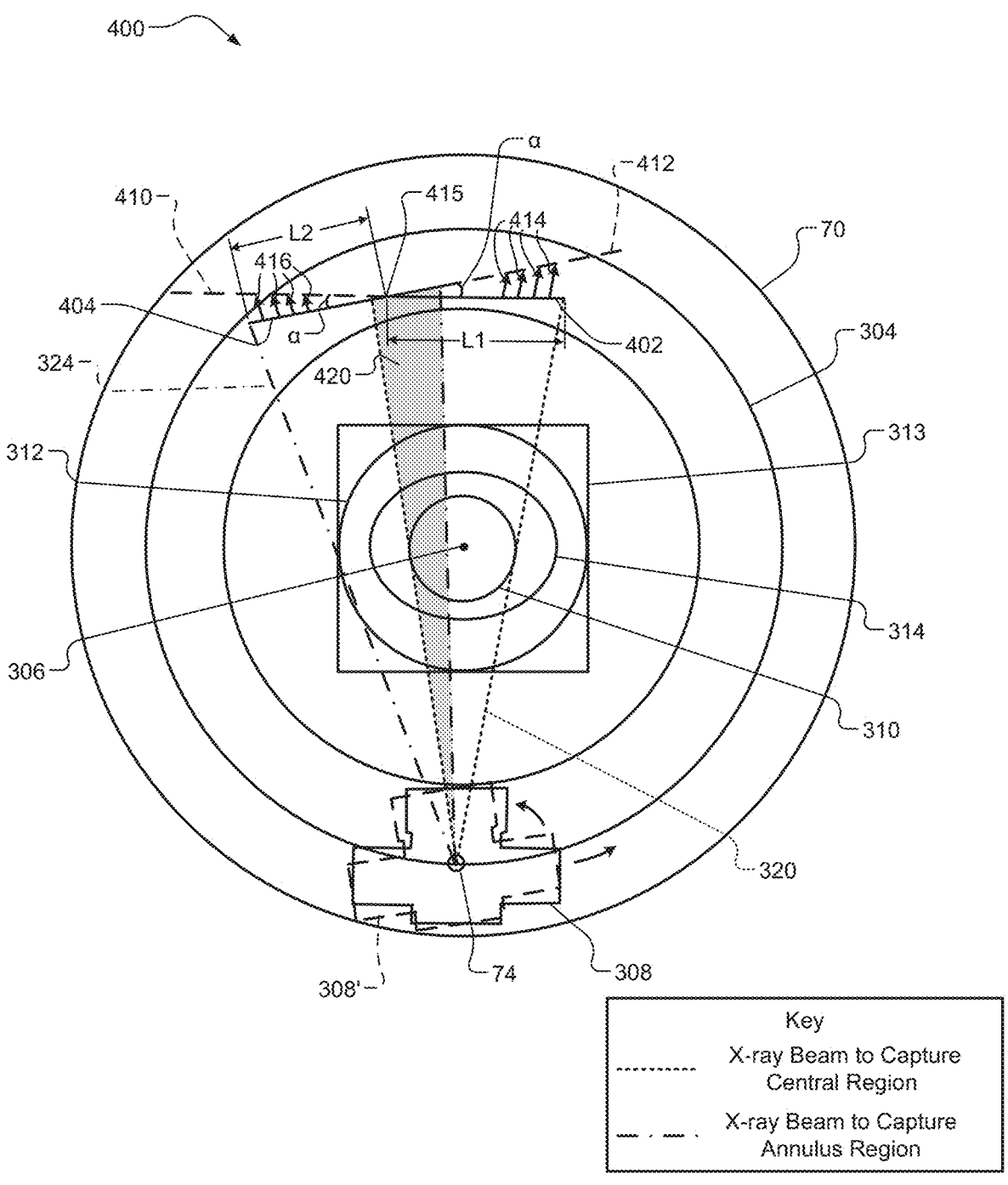
FIG. 4 is a cross-sectional view of a portion of the imaging system of FIG. 1 illustrating extended detector imaging planes for capturing images of central and annulus regions in accordance with the present disclosure.

In order to generate the increased FOV, two scans are performed; a first scan centered on the isocenter and capturing a center cylindrical (or center) region of the imaging volume, and a second scan not centered on the isocenter and capturing an annulus region around the central region. The first scan includes spinning the gantry a first time and capturing images of the central region while the X-ray source and detector array are rotated around the central region. The second scan includes initially rotating the X-ray source and detector array about the source focal point (point or area at which a high-percentage of X-rays are generated) and then spinning the gantry a second time and capturing images of the annulus region. The stated rotation about the focal point includes tilting the X-ray source and detector array and repositioning the detector array to capture the annulus region. The X-ray source and detector array are rotated around the annulus region while images of the annulus region are captured. An example of this is illustrated in FIGS. 3-4 and further described below.

Figure 8:
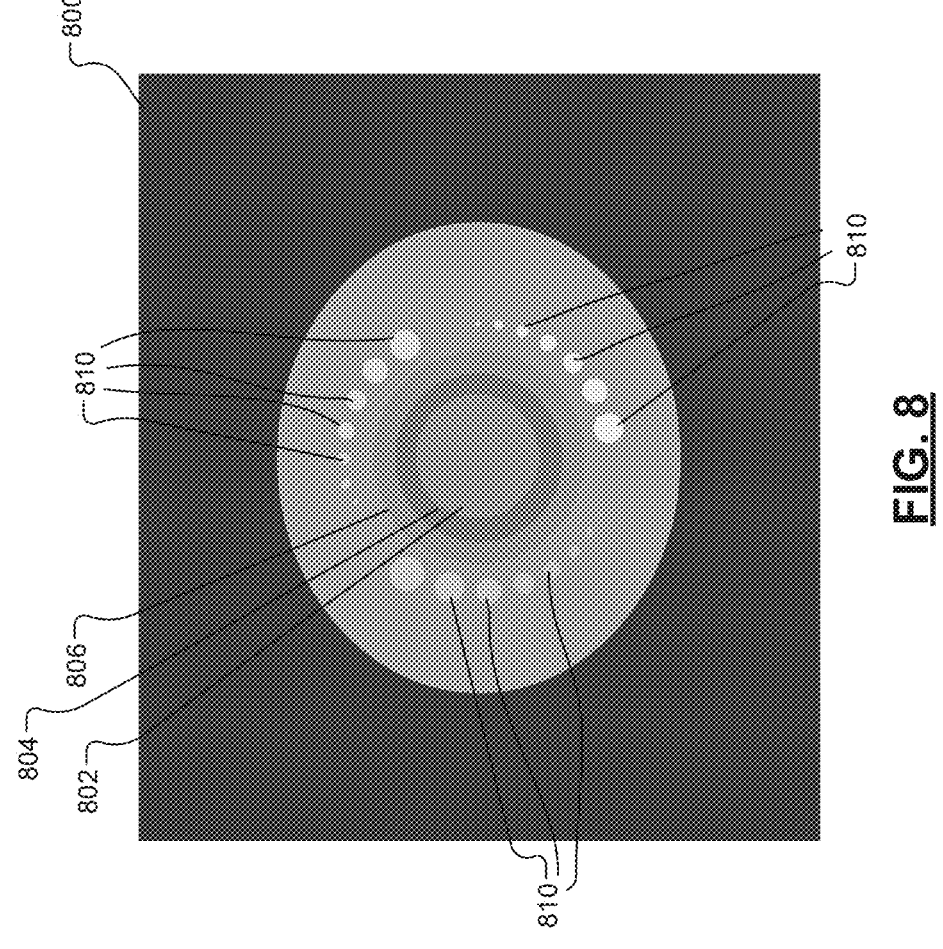
FIG. 8 is a reconstructed image generated based on the extended central region image and an annulus image of FIG. 7 implementing a back reconstruction method.

Combining of the image data collected from performing the central region scan and the image data collected from performing the annulus region scan using a back projection reconstruction method can result in artifacts. Example artifacts are shown in FIG. 8. The reconstruction of the collected data can yield artifacts corresponding to a captured overlap region (referred to as the "ring of overlap") of the two spins. This is the region that is captured twice during the two spins. The artifacts occur even after smoothly correcting for the double X-ray sampling of the overlap region. Other artifacts can occur and are attributed to disparities in image data processing, such as disparities between ramp filter outputs for image data collected for the two spin geometries; circular geometry for the central region and annular geometry for the annulus region. Some of the disparities are the result of a lack of agreement in the image data during use of image padding prior to the ramp filter application. The disagreement particularly occurs between 'corresponding' views of the two spins.

The views of the two spins are provided while the X-ray source is in the same location relative to the isocenter for both spins. For the first spin, the X-ray source may be oriented such that a centerline of an X-ray beam generated by the X-ray source passes through the isocenter of the imaging volume. In another embodiment, the centerline of the X-ray beam does not pass through and is offset from the isocenter, but the X-ray beam does cover the isocenter (i.e., the isocenter is in the image provided by the X-ray beam).

For the second spin, the X-ray source is tilted such that the centerline of the X-ray source beam is offset from the isocenter. For the second spin, the X-ray beam may not cover the isocenter. The detector array is in a first location relative to the isocenter and X-ray source for the first spin and in a second location relative to the isocenter and the X-ray source for the second spin. The first and second locations of the detector array refer to different radial distances from the isocenter and repositioning of the detector array to receive the X-ray beam from the X-ray source in the tilted orientation. Examples of these orientations and positions are shown in FIG. 4.

The examples set forth herein include a system and method for extended FOV imaging of an imaging volume (e.g., at least a portion of an aperture of a gantry where a subject to be imaged is located). The extended FOV imaging includes capturing i) a first set of images of a central region of the imaging volume, the first set of images being centered on the isocenter of the imaging volume, and ii) a second set of images of an annulus region of the imaging volume, the second set of images not being centered on the isocenter. Projected and interpolated padding data is generated for the first set of images based on the second set of images to provide first extended images. Padding data refers to data that is appended onto an image to extend the image. Padding data may include, for example, column edge data of an image that is repeated, projected and interpolated data, and/or other padding data disclosed herein. Projected and interpolated padding data is also generated for the second set of images based on the first set of images to provide second extended images. Generation of the projected and interpolated padding data includes performing a cone-beam projective transformation onto padding planes (or extended detector planes) for corresponding images as further described below. Extended reconstructed images of the imaging volume are then generated based on the first extended images and the second extended images.

Figure 1:
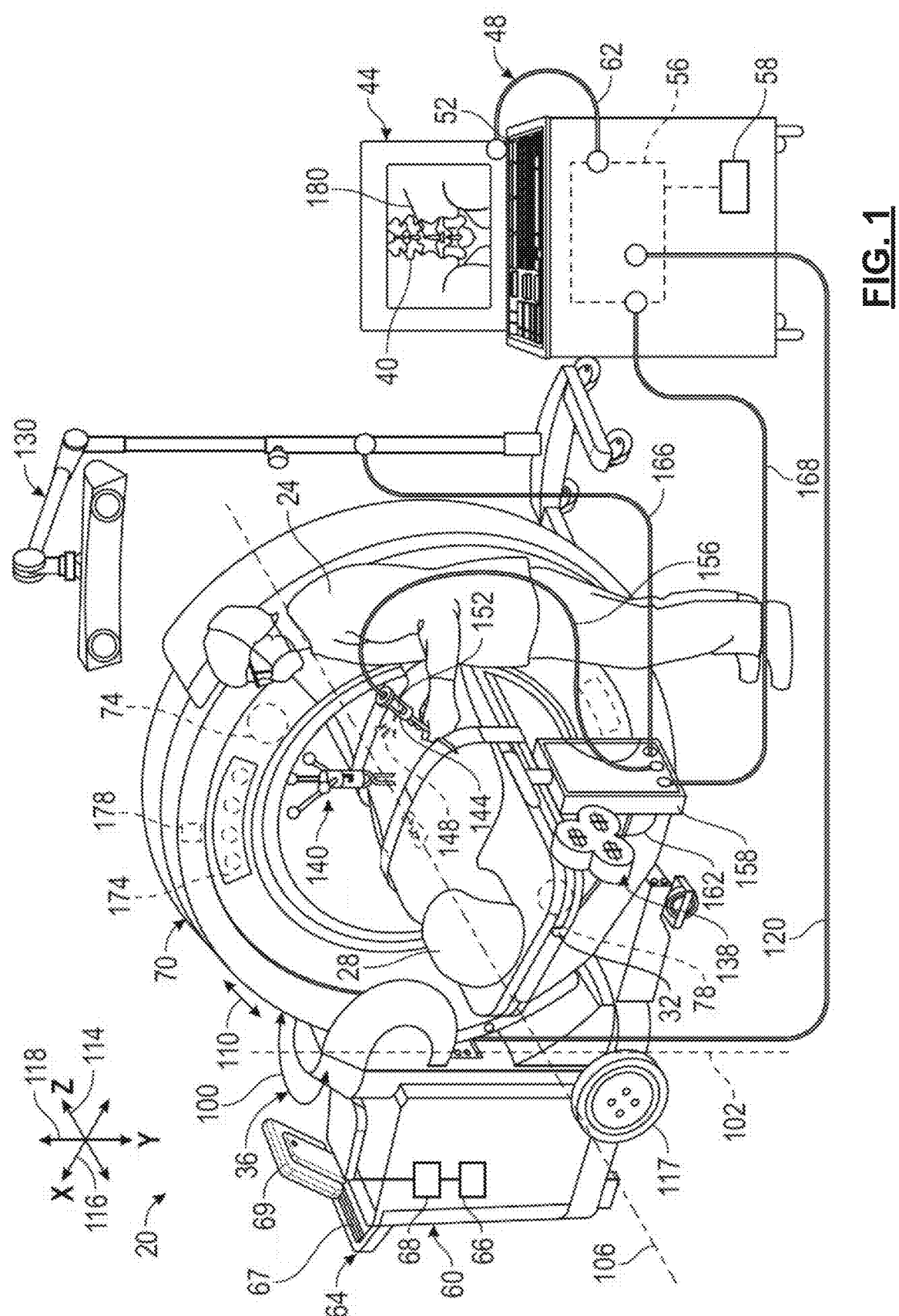
FIG. 1 is an environmental view of an operating theatre including an imaging system having a pre-back projection processing module in accordance with the present disclosure.

FIG. 1 shows a schematic view of a procedure room 20. A user 24, such as a surgeon, can perform a procedure on a subject, such as a patient 28. The subject may be placed on a support, such as a table 32 for a selected portion of the procedure. The table 32 may not interfere with image data acquisition with an imaging system 36. In performing the procedure, the user 24 can use the imaging system 36 to acquire image data of the patient 28 to allow a selected system to generate or create images to assist in performing a procedure. Images generated with the image data may be two-dimensional (2D) images, three-dimensional (3D), or appropriate type of images, such as a model (such as a three-dimensional (3D) image), long views, single projections views, etc. can be generated using the image data and displayed as an image 40 on a display device 44. The display device 44 can be part of and/or connected to a processing system 48 that includes a user interface 52, such as a keyboard, mouse, stylus, a touch screen as part of the display device 44 or combinations thereof. A processor 56, can include one or more processors, processor module, and/or microprocessors incorporated with the processing system 48 along with selected types of non-transitory and/or transitory memory 58. A connection 62 can be provided between the processor 56 and the display device 44 for data communication to allow driving the display device 44 to display or illustrate the image 40. The processor 56 may be any appropriate type of processor that executes instructions included in a program. The processor 56 may be an application specific processor such as an application specific integrated circuit.

The imaging system 36 can include but is not limited to an O-Arm® imaging system sold by Medtronic Navigation, Inc. The imaging system 36, including the O-Arm® imaging system, or other appropriate imaging systems may be in use during a selected procedure. Examples of O-Arm® imaging systems are described in U.S. Patent App. Pubs. 2012/0250822, 2012/0099772, and 2010/0290690, all the above incorporated herein by reference.

The imaging system 36, when, for example, including the O-Arm® imaging system, may include a mobile cart 60 that includes a controller and/or control system 64. The control system 64 may include a processor and/or processor 68 (similar to the processor 56), a user interface 67 such as a keyboard, a mouse, a touch screen, a memory 58 (e.g., a non-transitory memory) and a display device 69. The memory system 66 may include various instructions that are executed by the processor 68 that acts as a controller to control the imaging system 36, including various portions of the imaging system 36.

Figure 2:
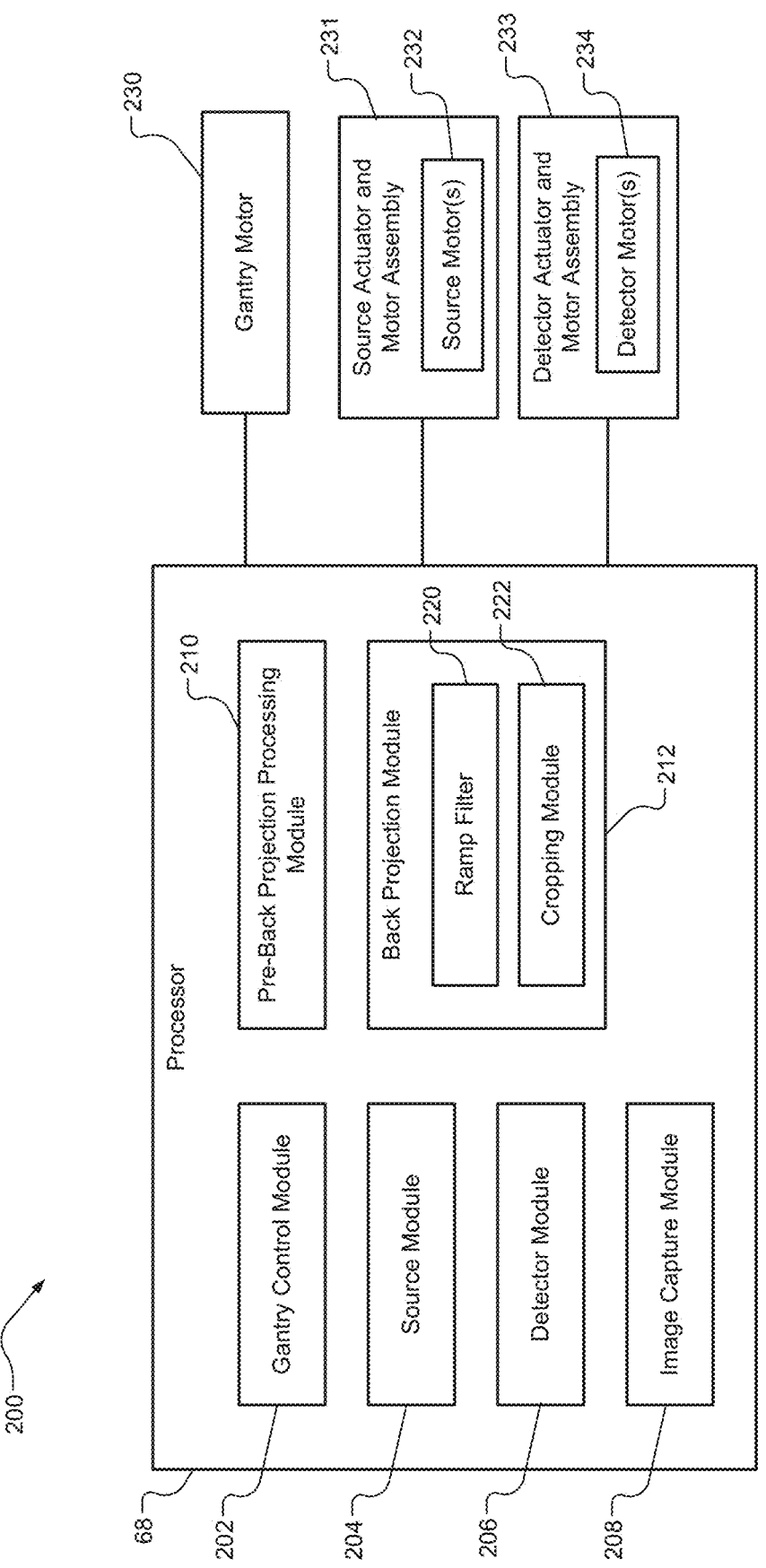
FIG. 2 is a functional block diagram illustrating a portion of the imaging system of FIG. 1 in accordance with the present disclosure.

The processor 56 and/or the processor 68 may include and/or execute a pre-back projection processing module. An example of the pre-back projection processing module is shown in FIG. 2 and is configured to perform corresponding portions of the method of FIG. 9. The pre-back projection processing module may perform, for example, operations 908, 910, 912, 914 of FIG. 9B.

The imaging system 36 may include further additional portions, such as a gantry 70 in which is positioned an X-ray source (also referred to as "a source assembly" or simply "the source") 74 and a detector array (also referred to as "a detector assembly" or simply "the detector") 78. In various embodiments, the detector 78 alone and/or together with the source unit may be referred to as an imaging head of the imaging system 36. The gantry 70 is moveably connected to the mobile cart 60. The gantry 70 may be O-shaped or toroid shaped, wherein the gantry 70 is substantially annular and includes walls that form a volume in which the source 74 and detector 78 may move. The mobile cart 60 may also be moved. In various embodiments, the gantry 70 and/or the mobile cart 60 may be moved while image data is acquired, including both being moved simultaneously. Also, the imaging system 36 via the mobile cart 60 can be moved from one operating theater to another (e.g., another room). The gantry 70 can move relative to the mobile cart 60, as discussed further herein. This allows the imaging system 36 to be mobile and moveable relative to the subject 28, thus allowing it to be used in multiple locations and with multiple procedures without requiring a capital expenditure or space dedicated to a fixed imaging system.

The processor 68 may be an application specific application processor. The memory system 66 may be a non-transitory memory such as a spinning disk or solid-state non-volatile memory. In various embodiments, the memory system may include instructions to be executed by the processor 68 to perform functions and determine results, as discussed herein. The memory system 66 may be used to store images from the imaging system 36 to allow calculations to be performed thereon. The memory system 66 may be used to store intermediate and final calculations, such as data for identifying body structures, distance for the imaging system to travel, a target position for the imaging system 36.

In various embodiments, the imaging system 36 may include an imaging system that acquires images and/or image data by the use of emitting X-rays and detecting X-rays after interactions and/or attenuations of the X-rays with or by the subject 28. The X-ray imaging may be an imaging modality. It is understood that other imaging modalities are possible, such as other high energy beams, etc.

Thus, in the imaging system 36, the source 74 may be an X-ray emitter that can emit X-rays at and/or through the patient 28 to be detected by the detector 78. As is understood by one skilled in the art, the X-rays emitted by the source 74 can be emitted in a cone along a selected main vector and detected by the detector 78. The source 74 and the detector 78 may also be referred to together as a source and detector assembly, especially wherein the source 74 is generally diametrically opposed (e.g., 180 degrees) (° apart) from the detector 78 within the gantry 70.

The imaging system 36 may move, as a whole or in part, relative to the subject 28. For example, the source 74 and the detector 78 can move around the patient 28, e.g., a 360° motion, spiral, portion of a circle, etc. The movement of the source and detector assembly within the gantry 70 may allow the source 74 to remain in a fixed position relative to the detector 78 during spinning of the gantry 70. Thus, the detector 78 may be referred to as moving around (e.g., in a circle or spiral) the subject 28 and it is understood that the source 74 remains opposed thereto, unless disclosed otherwise. The source 74 and the detector 78 may be tilted and moved relative to each other, as further described below.

Also, the gantry 70 can move isometrically (also referred as "wag") relative to the subject 28 generally in the direction of arrow 100 around an axis 102, such as through the mobile cart 60, as illustrated in FIG. 1. The gantry 70 can also tilt relative to a longitudinal axis 106 of the patient 28 illustrated by arrows 110. In tilting, a plane of the gantry 70 may tilt or form a non-orthogonal angle with the axis 106 of the subject 28.

The gantry 70 may also move longitudinally in the direction of arrows 114 along the axis 106 relative to the subject 28 and/or the mobile cart 60. Also, the mobile cart 60 may move to move the gantry 70. Further, the gantry 70 can move up and down generally in the Y-axis direction of arrows 118 relative to the mobile cart 60 and/or the subject 28, generally transverse to the axis 106 and parallel with the axis 102. The gantry may also be moved in an X direction in the direction of the arrows 116 by moving the wheels 117.

The movement of the imaging system 36, in whole or in part is to allow for positioning of the source and detector assembly relative to the subject 28. The imaging system 36 can be precisely controlled to move the source and detector assembly relative to the subject 28 to generate precise image data of the subject 28. The imaging system 36 can be connected to the processor 56 via a connection 120, which can include a wired or wireless connection or physical media transfer from the imaging system 36 to the processor 56. Thus, image data collected with the imaging system 36 can be transferred to the processor 56 for navigation, display, reconstruction, etc.

The source 74, as discussed herein, may include one or more sources of X-rays for imaging the subject 28. In various embodiments, the source 74 may include a single source that may be powered by more than one power source to generate and/or emit X-rays at different energy characteristics. Further, more than one X-ray source may be the source 74 that may be powered to emit x-rays with differing energy characteristics at selected times.

The imaging system 36 can be used with an un-navigated or navigated procedure. In a navigated procedure, a localizer and/or digitizer, including either or both of an optical localizer 130 and/or an electromagnetic localizer 138 can be used to generate a field and/or receive and/or send a signal within a navigation domain relative to the subject 28. The navigated space or navigational domain relative to the subject 28 can be registered to the image 40. Correlation, as understood in the art, is to allow registration of a navigation space defined within the navigational domain and an image space defined by the image 40. A patient tracker or dynamic reference frame (or registration device) 140 can be connected to the subject 28 to allow for a dynamic registration and maintenance of registration of the subject 28 to the image 40.

The patient tracking device or dynamic registration device 140 and an instrument 144 can then be tracked relative to the subject 28 to allow for a navigated procedure. The instrument 144 can include a tracking device, such as an optical tracking device 148 and/or an electromagnetic tracking device 152 to allow for tracking of the instrument 144 with either or both of the optical localizer 130 or the electromagnetic localizer 138. A navigation/probe interface 158 may have communications (e.g., wired or wireless) with the instrument 144 (e.g., via a communication line 156), with the electromagnetic localizer 138 (e.g., via a communication line 162), and/or the optical localizer 130 (e.g., via a communication line 166). The navigation/probe interface 158 can also communicate with the processor 56 with a communication line 168 and may communicate information (e.g., signals) regarding the various items connected to the navigation/probe interface 158. It will be understood that any of the communication lines can be wired, wireless, physical media transmission or movement, or any other appropriate communication. Nevertheless, the appropriate communication systems can be provided with the respective localizers to allow for tracking of the instrument 144 relative to the subject 28 to allow for illustration of a tracked location of the instrument 144 relative to the image 40 for performing a procedure.

The instrument 144 may be a ventricular or vascular stent, spinal implant, neurological stent or stimulator, ablation device, or the like. The instrument 144 may be an interventional instrument or can include or be an implantable device. Tracking the instrument 144 allows for viewing a location (including x,y,z position and orientation) of the instrument 144 relative to the subject 28 with use of the registered image 40 without direct viewing of the instrument 144 within the subject 28.

Further, the imaging system 36, such as the gantry 70, may include an optical tracking device 174 and/or an electromagnetic tracking device 178 to be tracked with the respective optical localizer 130 and/or electromagnetic localizer 138. Accordingly, the imaging system 36 can be tracked relative to the subject 28 as can the instrument 144 to allow for initial registration, automatic registration, or continued registration of the subject 28 relative to the image 40. Registration and navigated procedures are discussed in the above incorporated U.S. Pat. No. 8,238,631, incorporated herein by reference. Upon registration and tracking of the instrument 144, an icon 180 may be displayed relative to, including overlaid on, the image 40. The image 40 may be an appropriate image and may include a 2D image, a 3D image, or any appropriate image as discussed herein.

The source 74 may include a single assembly that may include a single X-ray tube. As discussed above, X-rays can be emitted from the X-ray tube generally in a cone shape towards the detector 78 and generally in the direction from the X-ray tube. An X-ray beam may be emitted as a cone or other appropriate geometry.

The subject 28 can be positioned within the X-ray cone to allow for acquiring image data of the subject 28 based upon the emission of X-rays in the direction of a vector towards the detector 78. The X-ray tube may be used to generate two-dimensional (2D) X-ray projections of the subject 28, including selected portions of the subject 28, or any area, region or volume of interest, in light of the X-rays impinging upon or being detected on a 2D or flat panel detector, as the detector 78. The 2D x-ray projections can be reconstructed, as discussed herein, to generate and/or display three-dimensional (3D) volumetric models of the subject 28, selected portion of the subject 28, or any area, region or volume of interest. As discussed herein, the 2D x-ray projections can be image data acquired with the imaging system 36, while the 3D volumetric models can be generated or model image data.

For reconstructing or forming the 3D volumetric image, appropriate techniques include filtered back projection, Expectation Maximization (EM), Ordered Subsets EM (OS-EM), Simultaneous Algebraic Reconstruction Technique (SART) and Total Variation Minimization (TVM), as generally understood by those skilled in the art. Various reconstruction techniques may also and alternatively include machine learning systems and algebraic techniques. The application to perform a 3D volumetric reconstruction based on the 2D projections allows for efficient and complete volumetric reconstruction. Generally, an algebraic technique can include an iterative process to perform a reconstruction of the subject 28 for display as the image 40. For example, a pure or theoretical image data projection, such as those based on or generated from an atlas or stylized model of a "theoretical" patient, can be iteratively changed until the theoretical projection images match the acquired 2D projection image data of the subject 28. Then, the stylized model can be appropriately altered as the 3D volumetric reconstruction model of the acquired 2D projection image data of the selected subject 28 and can be used in a surgical intervention, such as navigation, diagnosis, or planning. The theoretical model can be associated with theoretical image data to construct the theoretical model. In this way, the model or the image 40 can be built based upon image data acquired of the subject 28 with the imaging system 36.

The source 74 may include various elements or features that may be moved relative to the X-ray tube. In various embodiments, for example, a collimator may be positioned relative to the X-ray tube to assist in forming the cone relative to the subject 28. The collimator may include various features such as movable members that may assist in positioning one or more filters within the cone of the x-rays prior to reaching the subject 28. One or more movement systems may be provided to move all and/or various portions of the collimator. Further, as discussed further herein, various filters may be used to shape the x-ray beam, such as shaping the cone, into a selected shape prior to reaching the subject 28. In various embodiments, as discussed herein, the X-rays may be formed into a thin fan or plane to reach and pass through the subject 28 and be detected by the detector 78.

FIG. 2 shows a portion 200 of, for example, the imaging system 36 of FIG. 1. Although the portion 200 includes the processor 68, the processor 56 of FIG. 1 may be configured similarly. The processor 68 may include a gantry control module 202, a source module 204, a detector module 206, an image capture module 208, a pre-back projection processing module 210 and a back projection module 212. Each of the processors 68, 56 may be implemented as one or more processors. In one embodiment, the modules 202, 204, 206, 208, 210, 212 have corresponding code executed by the processor 68 and/or 56.

The back projection module 212 may include a ramp filter 220 and a cropping module 222 for performing the ramp filter and cropping operations disclosed herein. A ramp filter may be implemented as a convolution in the spatial domain or multiplication in the Fourier domain. The ramp filter is a image filter designed to reduce blurring caused by simple back projection. The ramp filter may include multiple filters such as a Ram-Lak filter, a noise-suppressing filter, and/or a sharpening filter. This may include implementing Sinc, Cosine, and/or Hamming functions. The ramp filter may be a high pass filter that does not permit low frequencies, which cause blurring to appear in an image. The ramp filter may be a compensatory filter that eliminates a star artifact resulting from simple back projection.

The processor 68 may be connected to and/or control a gantry motor 230, a source actuator and motor assembly 231 including one or more source motors 232, and/or detector actuator and motor assembly 233 including one or more detector motors 234. The gantry motor 230 may be configured to rotate a ring of the gantry on which the source 74 and detector 78 of FIG. 1 are mounted. The assemblies 231, 233 may include actuators, motors, brackets, linkages, pivot joints, rollers, bearings, etc. for orienting and positioning the source 74 and detector 78. The one or more source motors 232 may be used to tilt the source 74 and/or move the source 74 relative to an isocenter of an imaging volume, relative to the detector 78, and/or relative to another component and/or reference point of the imaging system 36. The one or more detector motors 234 may be used to tilt the detector 78 and/or move the detector 78 relative to the isocenter, relative to the source 74, and/or relative to another component and/or reference point of the imaging system 36. The stated control may be implemented by the modules 202, 204, and 206.

The image capture module 208 may control i) the capturing of images using the source 74 and the detector 78 of FIG. 1, and ii) the storing of image data. The pre-back projection processing module 210 may perform projecting and interpolating operations described herein, such as operations 908, 910, 912 and 914 of FIG. 9B. The back projection module 212 performs back projection to provide the extended and reconstructed FOV images disclosed herein. The ramp filter 220 performs ramp filtering operations, such as operation 918 of FIG. 9B. The cropping module 222 crops images as described with respect to operation 920 of FIG. 9B.

The following FIGS. 3-4 illustrate two spins as described above for capturing a first set of images for a central region and a second set of images for an annulus region and the geometries associated with each spin. The first spin is associated with the source 74 and detector 78 being oriented and in respective positions to capture the central region (i.e., circular region centered on isocenter and located within the imaging volume). The second spin is associated with the source 74 and detector 78 being oriented and in respective positions to capture the annuls region (i.e., annular region surrounding the central region, centered on the isocenter, and located within the imaging volume).

FIG. 3 shows a portion 300 of the imaging system 36 of FIG. 1. The imaging system 36 includes the gantry 70 having a housing 302 and a ring or rotor, represented as a circle 304. The source 74 and the detector 78 are mounted on and/or connected to the ring. The source 74 is able to be tilted relative to the ring, an isocenter 306, and the detector 78. The source 74 has a housing 308. The detector 78 is able to be tilted relative to the ring, the isocenter 306 and the source 74. The detector 78 is also able to be moved relative to the ring, isocenter 306 and source 74. This allows the source 74 and the detector 78 to be oriented and positioned to capture a first set of images of a central region 310 and a second set of images of an annulus region 312. The central region 310 is in the center of an imaging volume 313 of the gantry 70. The imaging volume 313 may correspond to at least a portion of the aperture (or opening) of the gantry 70 and refers to the FOV of interest. A cross-section of an example subject 314 is shown. Although the cross-section is shown centered on the isocenter 306, the subject 314 may not be centered within the imaging volume 313 and thus the cross-section may not be centered on the isocenter 306.

The source 74 and detector 78 are shown in two arrangements. The first arrangement shows the source 74 in a non-tilted state and generating a first X-ray beam 320 having a centerline 322 in alignment with and extending through the isocenter 306. The second arrangement shows the source 74' with housing 308' and the detector 78' in a tilted and an offset state and generating a second X-ray beam 324 having a centerline 326 offset from and not extending through the isocenter 306. During the first scan, the source 74 and detector 78 are maintained in the shown orientation and positions relative to each other and rotated 360° around the imaging volume 313. The source 74 and detector 78 follow the circle 304 when rotated while maintaining the centerline 322 passing through the isocenter 306. During the second scan, the source 74' and detector 78' are maintained in the shown orientation and positions relative to each other and rotated around the imaging volume 313 and follow the circle 304 while maintaining the centerline 326 in an offset state.

FIG. 4 shows a portion 400 of the imaging system 36 of FIG. 1 illustrating extended detector imaging planes for capturing images of the central region and the annulus region. In FIG. 4, the gantry 70 is shown including the ring represented by the circle 304, the source 74, and the imaging volume 313. The subject 314 is disposed in the imaging volume 313. The central region 310 and the annulus region 312 are shown and centered on the isocenter 306.

FIG. 4 illustrates geometries of corresponding views where the X-ray beam 320 is generated to provide images of the central region 310 and the X-ray beam 324 is generated to provide images of the annulus region 312. The X-ray source 74 may be in the same radial location or nearly the same radial location relative to the isocenter 306 for each of the X-ray beams 320, 324. The X-ray source 74 is not tilted for the first spin and a centerline of the X-ray beam 320 is aligned with and extends through the isocenter 306. The X-ray source 74 is tilted for the second spin such that the centerline of the X-ray beam 324 is offset from and does not extend through the isocenter 306.

The detector 78 is represented by a first detector plane (or detector surface) 402 for the first spin capturing the central region 310. The detector 78' is represented by a second detector plane (or detector surface) 404 for the second spin capturing the annulus region 312. During interpolated padding operations, such as operations 908 and 912 of FIG. 9B, the first detector plane 402 is extended to provide a first extended portion, as represented by dashed line 410. The second detector plane 404 is also extended to provide a second extended portion, as represented by dashed line 412.

Figure 10:
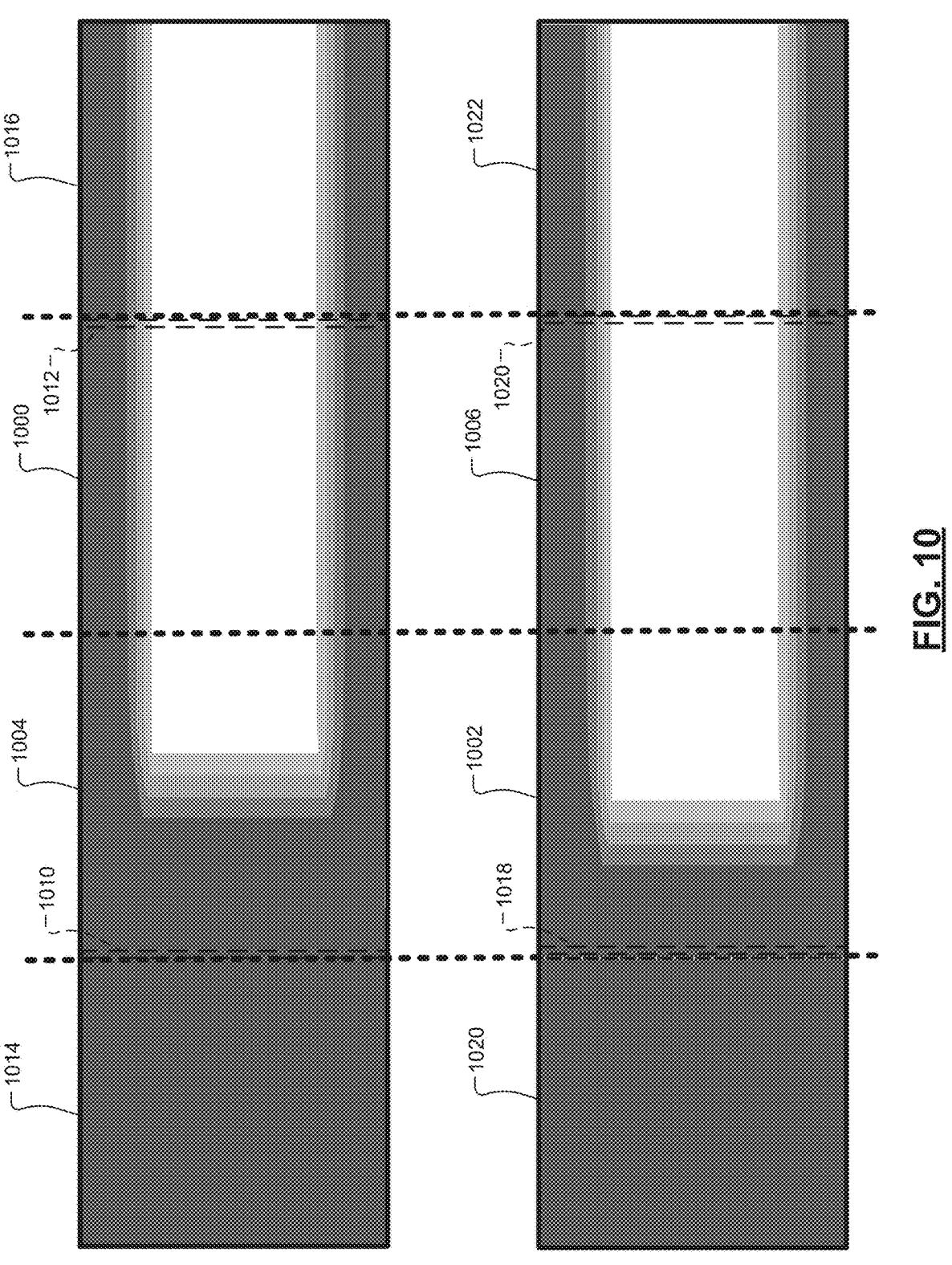
FIG. 10 is an image diagram illustrating extended central region and annulus region images including interpolated padding portions and additional padding portions in accordance with the present disclosure.

Image data that is collected in association with the first detector plane 402 is interpolated and projected onto the second extended portion 412 of the second detector plane 404. This projection is represented by arrows 414 and may be based on first geometrical dimensions such as i) a length L1 of at least a portion of the first detector plane 402 measured from a point 415 of intersection between the planes 402, 404, and ii) an angle α between the first detector plane 402 and the second extended portion 412 of the second detector plane 404. Image data that is collected in association with the second detector plane 404 is interpolated and projected onto the first extended portion 410 of the first detector plane 402. This projection is represented by arrows 416 and may be based on second geometrical dimensions such as a length L2 of at least a portion of the second detector plane 404 measured from the point 415 of intersection between the planes 402, 404 and the angle α between the second detector plane 404 and the first extended portion 410 of the first detector plane 402. This provides extended detector images as further described below and as shown in FIG. 10.

An overlap area 420 is shown, which refers to an area of overlap of the X-ray beams 320, 324. The overlap area 420 is defined by the X-ray beams 320, 324 and the detector planes 402, 404. The rays contributing to overlap area 420 are reweighted during back projection to account for the redundant ray-sampling in this region, such as during operation 922 of FIG. 9B. In an embodiment, the reweighting is done in a smooth manner including changing weights from, for example, a 1 for certain data to a value between 0 and 1. The image data for the portion of the X-ray beam 320 that overlaps the X-ray beam 324 and is closest to the centerline of the X-ray beam 320 is weighted highest (e.g., weighted with (or multiplied by) a 1) towards a centerline of the X-ray beam 320 and lowest (e.g., weighted with (or multiplied by) a 0) towards the edge of the X-ray beam 320 that overlaps the X-ray beam 324. Similarly, the image data for the portion of the X-ray beam 324 that overlaps the X-ray beam 320 is weighted highest (e.g., weighted with (or multiplied by) towards a centerline of the X-ray beam 324 and lowest (e.g., weighted with (or multiplied by) a 0) towards the edge of the X-ray beam 324 that overlaps the X-ray beam 320. A gradient of weighting between 0-1 is used for the overlap portions of each of the X-ray beams 320, 324. In an embodiment and for each of the pixels corresponding to a portion of a reconstructed image associated with the overlap region, the weight of image data corresponding to X-ray beam 320 and the weight of image data corresponding to X-ray beam 324 adds up to 1.

Figure 7:
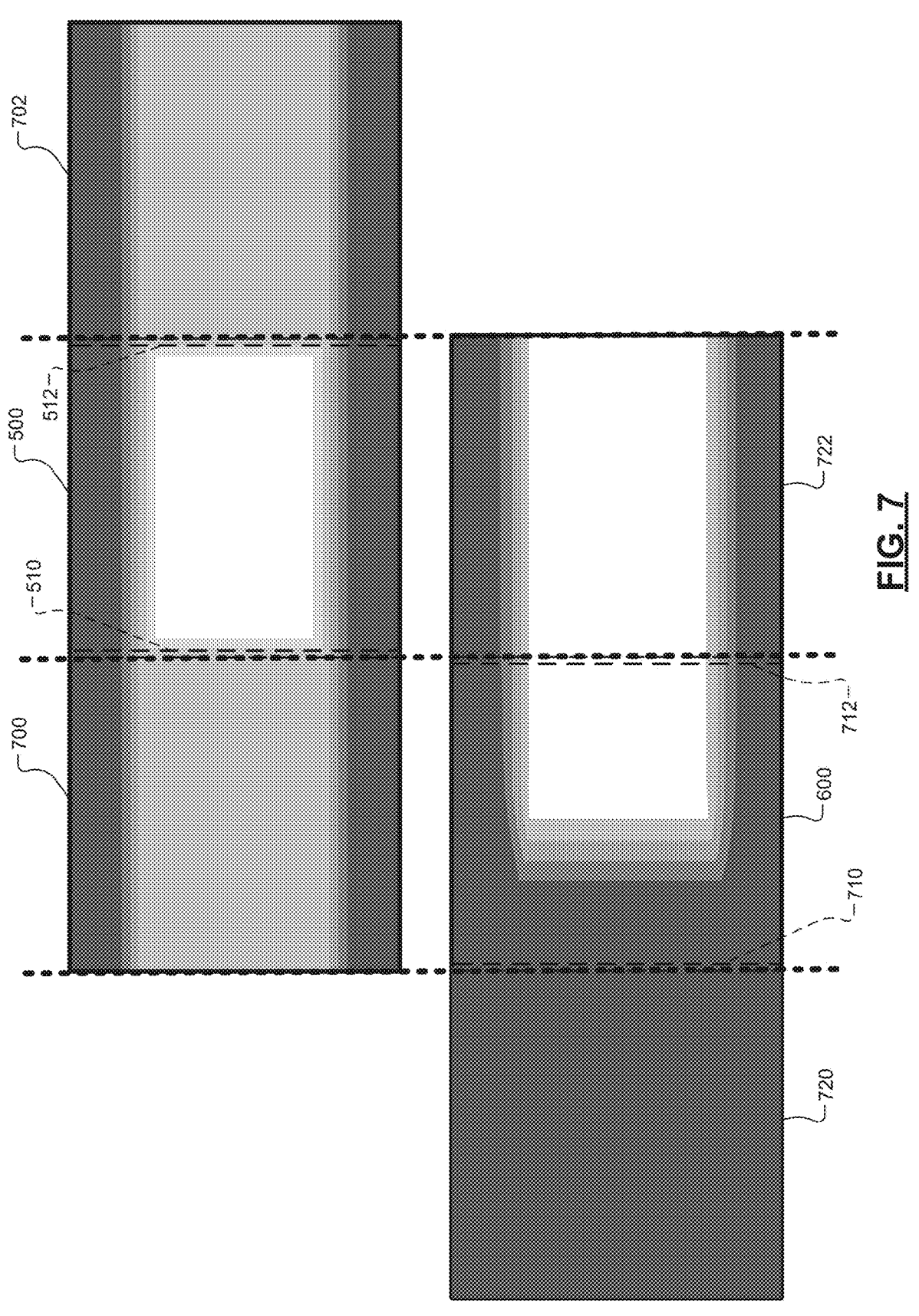
FIG. 7 is an image diagram illustrating differences between padding of an extended central region image and an annulus image.

In FIG. 4, the extended portions 410, 412 of the planes 402, 404 correspond to padding regions having data inconsistent (or different) than data associated with the planes 402, 404. The padding data is generated during the interpolated projection operations and used during back projection to minimize and/or eliminate artifacts associated with differences between i) padding data of an image of the central region 310 and ii) an image of a portion of the annulus region 312. An example of these differences is shown in FIG. 7. The padding regions are shown for two views. The first view is associated with the source 74 and detector 78 being in the first orientation and respective positions for capturing an image of the central region 310. The second view is associated with the source 74 and detector 78 being in the second orientation and respective positions for capturing an image for the annulus region 312.

Each of the following described FIGS. 5-8 and 10-11 includes a certain number of changes in shading to illustrate variations in brightness of images between bright and dark portions of the images. Although each of these figures includes a certain number of shaded variations (or changes in brightness), each image may include any number of shaded variations between the brightest and darkest portions of the images.

Figure 5:
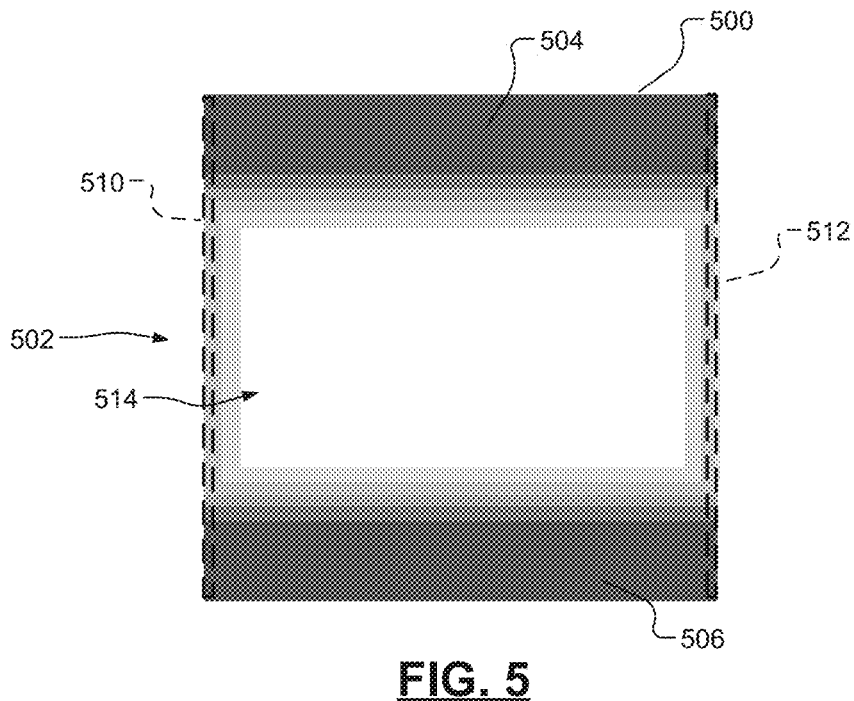
FIG. 5 is an image of a central region with the source and detector in first orientations and positions.

Referring now to FIGS. 3 and 5, an example image 500 of the central region 310 is shown with the source 74 and detector 78 in first orientations and positions. The image includes: a light central area 502 corresponding to the subject 314 in the central region 310; and a dark upper area 504 and a dark lower area 506 corresponding to areas in the imaging volume 313 above and below the subject 314. The areas in the imaging volume 313 above and below the subject 314 include portions of the annulus region 312. The central area 502 varies in brightness towards the upper and lower areas 504, 506 and side edges 510, 512 of the image 500. The brightness of the central area 502 decreases in brightness towards the upper and lower areas 504, 506 and edges 510, 512. The edges 510, 512 are brighter than a center portion 514 of the central area 502.

Figure 6:
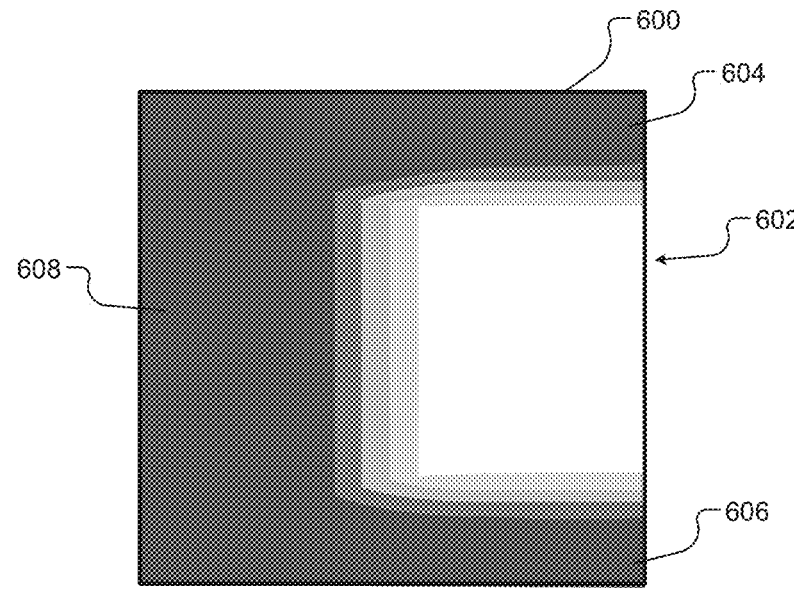
FIG. 6 is an image of an annulus region with the source and detector in second orientations and positions.

Referring now to FIGS. 3 and 6, an example image 600 of the annulus region 312 is shown with the source 74 and detector 78 in second orientations and positions. The image includes: a center area 602 corresponding to an outer portion of the subject 314 in the central region 310 of FIG. 3; and an dark upper area 604, a dark lower area 606, and a dark outer (or side) area 608 corresponding to areas in the imaging volume 313 above, below and on a side of the subject 314. The areas in the imaging volume 313 above, below and on a side of the subject 314 include respective portions of the annulus region 312. The center area 602 varies in brightness towards the side area 608 of the image 500. The brightness of the central area 502 decreases in brightness towards the areas 604, 606 and 608.

FIG. 7 shows an image diagram illustrating differences between padding of an extended central region image and an annulus image. One method of reconstructing an extended FOV image is to add padding onto the images 500, 600, ramp filter the resulting extended images, crop the filtered extended images and perform back projection to provide an extended reconstructed image of the imaging volume 313. Generation of padding data for image 500 includes determining vertical pixel side edge data (e.g., color and brightness of each pixel in first and last column of image 500) at the side edges 510, 512 of the image 500 and repeating that data laterally outward, as shown, to provide extended padding portions 700, 702. The pixel data in extended padding portions 700, 702 match pixel data along the side edges 510, 512. This is similarly done for the image 600, where vertical pixel side edge data of side edges 710, 712 (e.g., first and last columns) of the image 600 are repeated laterally outward to provide extended padding portions 720, 722. The pixel data in extended padding portions 720, 722 match pixel data along the side edges 710, 712.

The above-described padding process, which provides the padding data of FIG. 7, may be performed for each pair of images generated for the central region 310 and the annulus region 312. Each resulting extended pair of images may be filtered and cropped and the resulting filtered and cropped images are back projected to provide a resulting reconstructed image. As an example, a ramp filter may be used to filter the extended resulting pair of images. As an example, a Feldkamp, Davis and Kress (FDK) filtered back projection algorithm may be used to perform the back projection. A FDK filtered back projection algorithm may be used for three-dimensional reconstruction from the cone-beam projections of the regions 310, 312 and measured with circular orbit of an X-ray source and a detector array. The FDK algorithm may include filtering and cropping as disclosed herein.

As can be seen in FIG. 7 there is a disagreement (or differences) between the padding portion 700 and the image 600. Because of these differences, artifacts are generated during the back projection process. Examples of these artifacts are shown in FIG. 8. This is because the described padding leads to a disagreement among the edge information in the padding portion 700 and the image 600 prior to the ramp filter computation, which leads to ring artifacts in the final reconstructed image, as shown in FIG. 8.

FIG. 8 shows a reconstructed image 800 generated based on the extended central region image generated based on at least the image 500 and padding portion 700 of FIG. 7 and the annulus image 600 of FIG. 7. The reconstructed image 800 includes artifacts 802, 804, 806. Artifact 804 is referred to as a ring artifact and is associated with differences between pixel data at and near the edges 510 and 712.

In FIG. 8, contrast inserts, some of which are designated 810, are shown. The contrast inserts 810 are used as an image phantom during simulation for image reconstruction testing. The contrast inserts 810 are simulated as actually being in the corresponding imaging volume and are used as references to evaluate reconstructed image quality. Image data of the contrast inserts 810 is included in the raw image data of the imaging volume. The contrast inserts 810 aid in differentiating different image intensities and visualizing differences in contrast levels. The example contrast inserts 810 increase in brightness around the center of the imaging volume. As an example, the contrast inserts 810 may increase in brightness 5-10% from insert-to-insert. The more noise, the more difficult it is to see the contrast inserts 810 in the reconstructed image. The worse the contrast inserts look, the poorer the image quality.

Figure 9A:
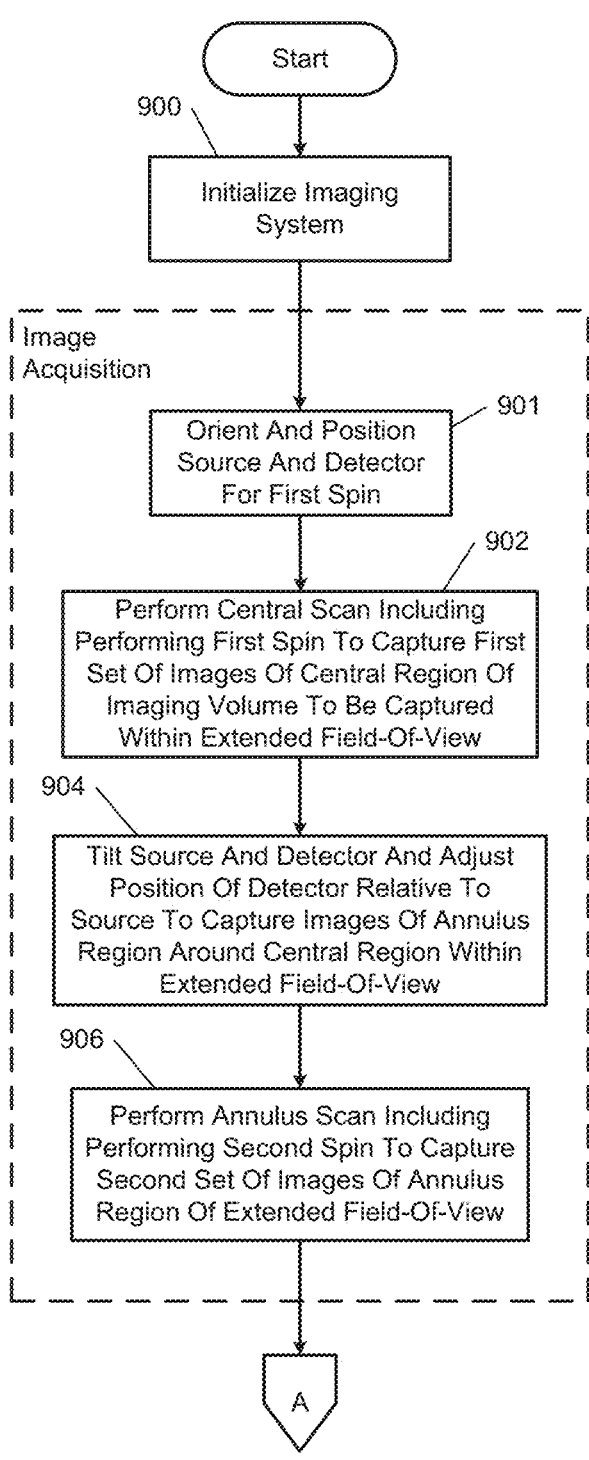
FIGS. 9A and 9B (collectively FIG. 9) illustrate an extended FOV image reconstruction method including pre-back projection processing in accordance with the present disclosure.
Figure 9B:
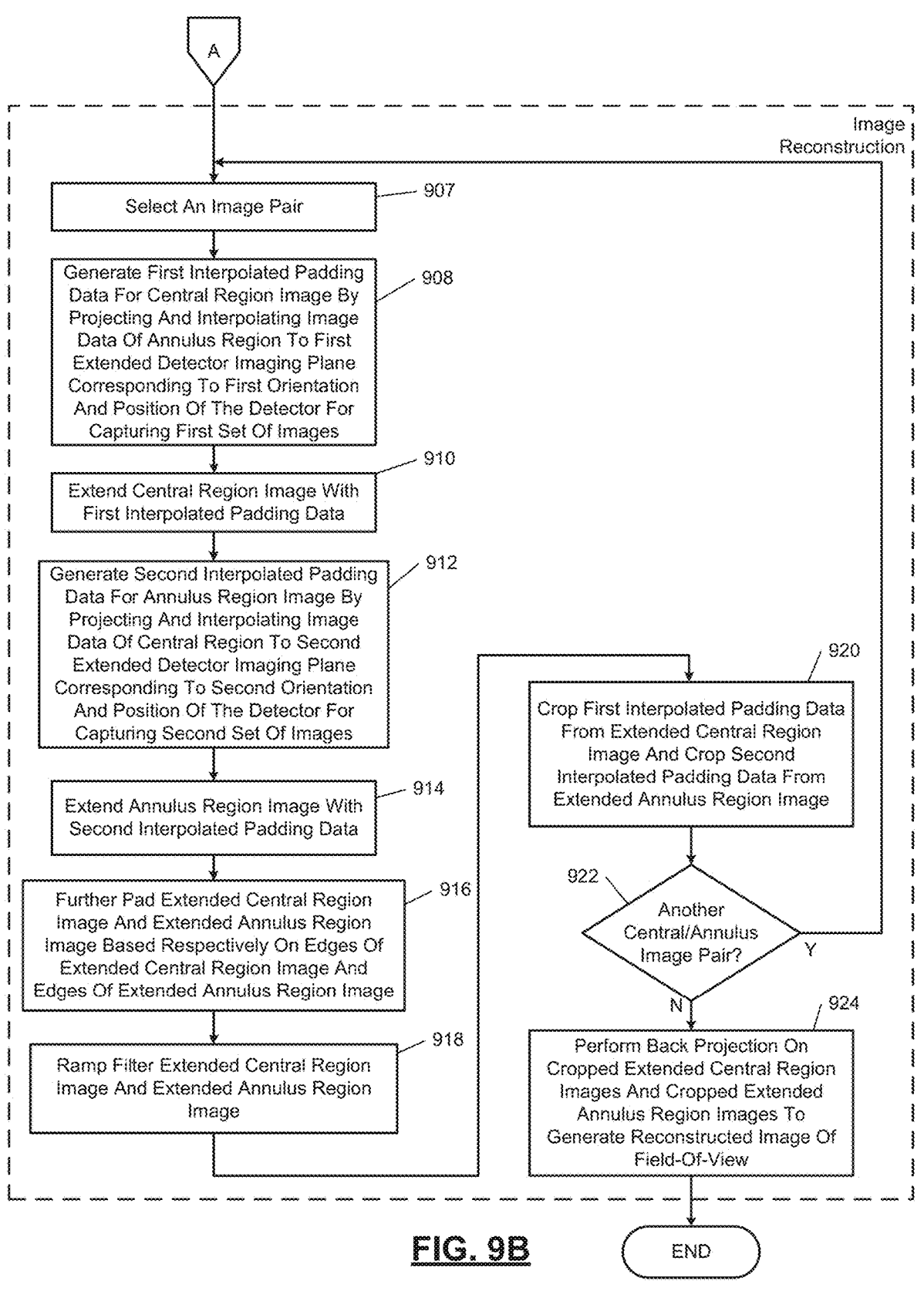

FIGS. 9A and 9B (collectively FIG. 9) illustrate an extended FOV image reconstruction method including pre-back projection processing in accordance with the present disclosure. The method may be performed by a processor (e.g., one of the processor referred to herein) and implemented by an imaging system (e.g., the imaging system 36 of FIG. 1). The operations may be iteratively performed.

At 900, the processor initializes the imaging system. This may include determining orientations and positions of the X-ray source and a detector array, setting an image capturing frequency, setting a gantry rotation speed, downloading pre-back projection processing instructions and/or other imaging instructions, etc.

The following operations 901, 902, 904, 906 are part of an image acquisition process. At 901, the processor orients and positions X-ray source and detector array for first spin. At 902, the processor performs a central (first) scan including performing a first spin of the gantry to capture a first set of images of the central region of the imaging volume. An example image included in the first set of images is designated 1000 in FIG. 10.

At 904, the processor tilts X-ray source and detector array and adjusts position of the detector array relative to the X-ray source to capture images of annulus region around central region within extended field-of-view. At 906, the processor performs annulus scan including performing second spin to capture second set of images of annulus region of extended field of view. The second set of images are correlated with the first set of images to provide image pairs. An example image included in the second set of images is designated 1002 in FIG. 10.

At 907, the processor selects one of the image pairs (i.e., a first image pair or a next image pair) including a respective one of the first set of images and a respective one of the second set of images.

At 908, the processor generates first projected and interpolated padding data for the central region image by projecting and interpolating image data of the annulus region to the first extended detector imaging plane corresponding to first orientation and position of the detector array for capturing the first set of images. The annulus region image data is used to generate the first projected and interpolated padding data for the central region image by projecting image data on the first detector plane to image data on the extended portion of the second detector plane, as described above. This is represented by arrows 416 of FIG. 4. Example first projected and interpolated padding data is shown as extended image portion 1004 of FIG. 10. In the current implementation, the geometric projection is performed by iterating through each pixel in the padding region of the first scan and defining the ray between this point and the source focal spot. A ray-plane intersection calculation is then performed between this ray and the plane that defines the position of the receiving surface of the detector for the corresponding image view of the second scan. The intensity at the ray-plane intersection is extracted using an interpolation approach (e.g., a nearest neighbor interpolation algorithm or a bilinear interpolation algorithm). The padding pixel's intensity value in the first scan is then set to be this interpolated value. At 910, the processor extends central region image with the first projected and interpolated padding data. Operations 908, 910 are represented by arrows 416 of FIG. 4.

At 912, the processor generates second projected and interpolated padding data for the annulus region image by projecting and interpolating image data of the central region to the second extended detector imaging plane corresponding to the second orientation of the detector array for capturing the second set of images. The central region image data is used to generate the second projected and interpolated padding data for the annulus region image by projecting image data on the second detector plane to image data on the extended portion of the first detector plane, as described above. In the current implementation, the geometric projection is performed by iterating through each pixel in the padding region of the second scan and defining the ray between this point and the source focal spot. A ray-plane intersection calculation is then performed between this ray and the plane that defines a position of the receiving surface of the detector of the corresponding image view of the first scan. The intensity at the ray-plane intersection is extracted using an interpolation approach (e.g., a nearest neighbor interpolation algorithm or a bilinear interpolation algorithm). The padding pixel's intensity value in the second scan is then set to be this interpolated value. At 914, the processor extends annulus region image with the second projected and interpolated padding data. Example second projected and interpolated padding data is shown as extended image portion 1006 of FIG. 10.

At 916, the processor further pads the extended central region image and the extended annulus region image. Edges 1010, 1012 of the extended central region image, which includes image 1000 and first projected and interpolated padding data 1004, are repeated outward from the edges 1010, 1012 to provide extended regions 1014, 1016. Edges 1018, 1020 of the extended annulus region image, which includes image 1002 and second projected and interpolated padding data 1006, are repeated outward from the edges 1018, 1020 to provide extended regions 1020, 1022.

At 918, the processor ramp filters i) the resultant extended central region image, which includes the image 1000, the first projected and interpolated padding data 1004, and the additional padding data 1014, 1016, and ii) the image 1002, the second projected and interpolated padding data 1006, and the additional padding data 1020, 1022. The ramp filter (e.g., ramp filter 220) outputs a filtered extended central region image and a filtered extended annulus region image. The ramp filter reduces blurring of reconstructed image.

At 920, the processor may crop the filtered extended central region image and a filtered extended annulus region image to remove, for example, filtered padded regions associated with the padded data 1014, 1016, 1020, 1022 of FIG. 10. In an embodiment, all padded regions are cropped.

At 922, the processor determines whether another central and annulus image pair is to be processed. If yes, operation 908 may be performed, otherwise 924 may be performed.

At 924, the processor may perform back projection on the cropped filtered extended central region images and the cropped filtered extended annulus region images to generate a reconstructed image of FOV. This may include using a FDK back projection algorithm. The back projection module 212 may, for example, take images and back project through the imaging volume and for each pixel along a line back to the source and for every voxel the line intersects, add the corresponding pixel values. The back projection module 212 "smears" data in an additive fashion to the reconstructed voxels. This is done for each detector position. All pixel data values for the detector being in the first position relative to the source for the first spin and where there are intersections with voxels are summed back to the source. All pixel data values for the detector being in the second position relative to the source for the second spin and where there are intersections with voxels are summed back to the source. Each voxel refers to a three-dimensional space within the imaging volume. The imaging volume may include, for example, 512×512×512 voxels or, in other words, 512 voxels along each vertical, horizontal, and depth side edge of the imaging volume, where the imaging volume has a shape of a cube.

In an embodiment, the back projection includes reweighting of overlapping image data, as described above. The FDK algorithm performs reweighting to account for the double ray sampling region of overlap. An example of the overlap region is shown in FIG. 4. The method may end subsequent to operation 924.

In an embodiment, all projection images from both scans are padded, then ramp filtered, then cropped to original dimensions, and then back projected iteratively, one by one. The projected images are all back projected onto the same volume to form the collective total reconstruction (or reconstructed image). The one-by-one (or pair-by-pair) processing is an example implementation. The processing may be done in a manner where all images are padded in the same stage, etc. The back-projection process is a linear operation. Thus, the order of which the projections are received can be changed.

The above-described method includes implementations of algorithms to improve the processing of captured image data to provide better quality extended FOV images with minimal or no artifacts. The algorithms can also improve contrast variations of the images for improved image clarity. The method may be implemented during a simulation to test quality of image reconstruction and/or during actual use to improve image reconstruction. Reconstructed images are then able to be displayed, analyzed, compared, and/or evaluated as described above to detect and diagnose issues with one or more scanned subjects.

In the above method, the padding data is computed by using the image data from edges of two corresponding images. The central region image has its padding region determined by a projective interpolation of its corresponding annulus region image. As shown in FIG. 4, the padded region for the central region image is taken as an extension of its current imaging plane, and the corresponding annulus region image data is projected and interpolated onto the padded region (under a cone-beam projection geometry) of the central region image. This is then repeated for the annulus image. The resulting padding can be seen in FIG. 10.

Figure 11:
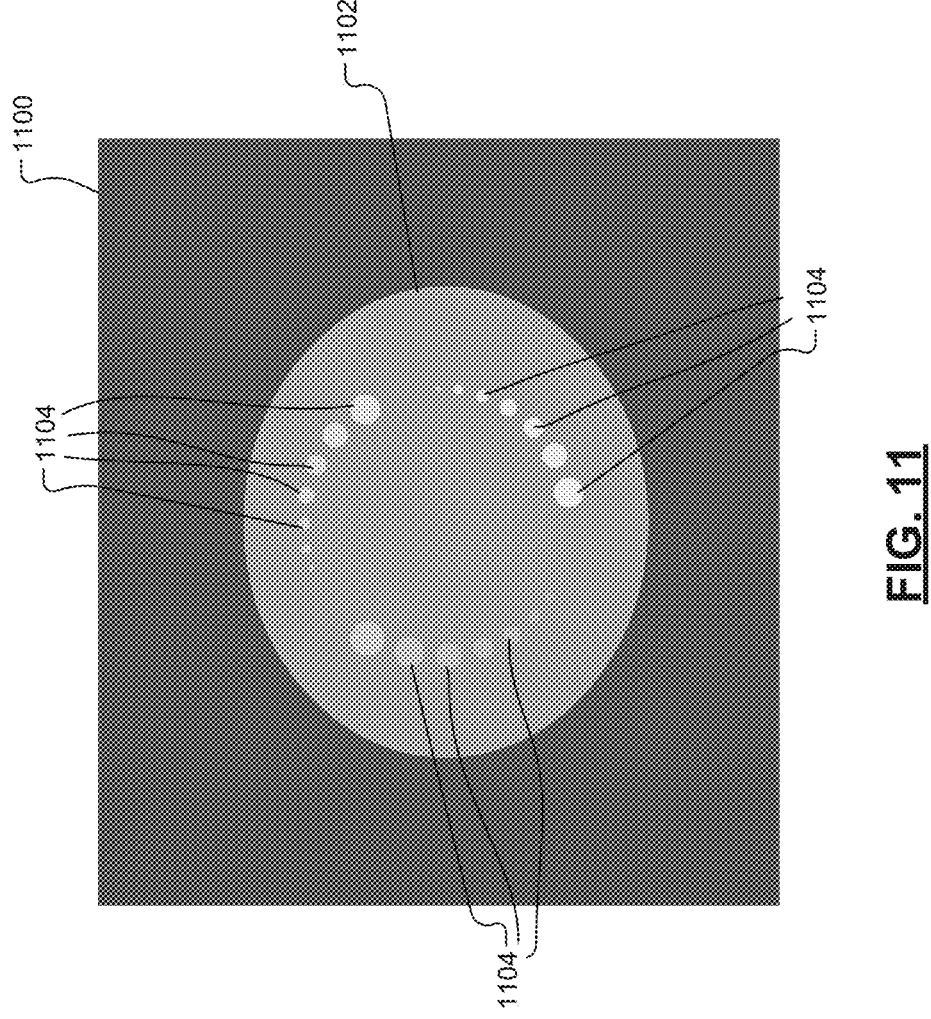
FIG. 11 is a reconstructed image generated based on the extended central region image and an annulus region image of FIG. 10 implementing a back projection reconstruction method in accordance with the present disclosure.

FIG. 11 shows a reconstructed image 1100 generated based on the extended central region image and extended annulus region image of FIG. 10 implementing a back projection reconstruction method. The reconstructed image 1100 includes a bright inner portion 1102, corresponding to the annulus and central regions, and contrast inserts 1104. The contrast inserts 1104 may be the same as the contrast inserts 810 of FIG. 8.

The above-described method of FIG. 9 includes the use of image information from other projections to pad a current image. The method also includes determining padding using a cone-beam projective transformation onto a padding (or extended detector) plane of corresponding images. By extending the image FOV as disclosed herein many workflow challenges are able to be solved in an operating room, where it is difficult to center a patient on an isocenter.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

Instructions may be executed by a processor and may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The apparatuses and methods described in this application may be partially or fully implemented by one or more processors (also referred to as processor modules) that may include a special purpose computer (i.e., created by config-uring one or more processors) to execute one or more particular functions embodied in computer programs. The computer programs include processor-executable instruc-tions that are stored on at least one non-transitory, tangible computer-readable medium. The computer programs may also include or rely on stored data. The computer programs may include a basic input/output system (BIOS) that inter-acts with hardware of the special purpose computer, device drivers that interact with particular devices of the special purpose computer, one or more operating systems, user applications, background services and applications, etc.

The computer programs may include: (i) assembly code; (ii) object code generated from source code by a compiler; (iii) source code for execution by an interpreter; (iv) source code for compilation and execution by a just-in-time com-piler, (v) descriptive text for parsing, such as HTML (hyper-text markup language) or XML (extensible markup lan-guage), etc. As examples only, source code may be written in C, C++, C#, Objective-C, Haskell, Go, SQL, Lisp, Java®, ASP, Perl, Javascript®, HTML5, Ada, ASP (active server pages), Perl, Scala, Erlang, Ruby, Flash®, Visual Basic®, Lua, or Python®.

Communications may include wireless communications described in the present disclosure can be conducted in full or partial compliance with IEEE standard 802.11-2012, IEEE standard 802.16-2009, and/or IEEE standard 802.20-2008. In various implementations, IEEE 802.11-2012 may be supplemented by draft IEEE standard 802.11ac, draft IEEE standard 802.11ad, and/or draft IEEE standard 802.11ah.

A processor, processor module, module or 'controller' may be used interchangeably herein (unless specifically noted otherwise) and each may be replaced with the term 'circuit.' Any of these terms may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

Instructions may be executed by one or more processors or processor modules, such as one or more digital signal processors (DSPs), general purpose microprocessors, appli-cation specific integrated circuits (ASICs), field program-mable logic arrays (FPGAs), or other equivalent integrated or discrete logic circuitry. Accordingly, the term "processor" or "processor module" as used herein may refer to any of the foregoing structure or any other physical structure suitable for implementation of the described techniques. Also, the techniques could be fully implemented in one or more circuits or logic elements.

The foregoing description of the embodiments has been provided for purposes of illustration and description. It is not intended to be exhaustive or to limit the invention. Indi-vidual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A method of reconstructing an extended field-of-view image of an imaging volume of a gantry of an X-ray imaging system, the method comprising:
performing a first spin of the gantry to capture a first set of images of a central region of the imaging volume;
performing a second spin of the gantry to capture a second set of images of an annulus region of the imaging volume surrounding the central region;
generating first projected and interpolated padding data for a first image of the central region based on a first image of the annulus region, the first set of images comprising the first image of the central region, and the second set of images comprising the first image of the annulus region;
generating a first extended image of the central region based on the first projected and interpolated padding data;
generating second projected and interpolated padding data for the first image of the annulus region based on the first image of the central region;
generating a first extended image of the annulus region based on the second projected and interpolated padding data;
padding the first extended image of the central region based on edge pixel data of the first extended image of the central region;
padding the first extended image of the annulus region based on edge pixel data of the first extended image of the annulus region; and
performing back projection to reconstruct the extended field-of-view image of the imaging volume based on the first extended image of the central region and the first extended image of the annulus region.

2. The method of claim 1, wherein the central region of the imaging volume is centered on an isocenter of the gantry.

3. The method of claim 1, wherein:
the central region of the imaging volume is not centered on an isocenter of the gantry; and
the isocenter is included in each of the first set of images.

4. The method of claim 1, further comprising:
orienting and positioning an X-ray source and a detector array to capture the first set of images; and
reorienting and repositioning the X-ray source and the detector array to capture the second set of images.

5. The method of claim 1, further comprising, subsequent to padding, ramp filtering the first extended image of the central region and the first extended image of the annulus region.

6. The method of claim 1, wherein:
generating the second projected and interpolated padding data comprises projecting and interpolating image data on a first detector plane, associated with a detector array of the gantry being in a first orientation and position for capturing the first set of images, to an extended portion of a second detector plane associated with the detector array being in a second orientation and position for capturing the second set of images; and generating the first projected and interpolated padding data comprises projecting and interpolating image data on the second detector plane to an extended portion of the first detector plane.

7. The method of claim 1, wherein:

generating the second projected and interpolated padding data comprises a geometric projection onto an extended portion of a first detector plane, the first detector plane corresponding to a detection surface of a detector array of the gantry in a first orientation and a first position; and generating the first projected and interpolated padding data comprises a geometric projection onto an extended portion of a second detector plane, the second detector plane corresponding to the detection surface of the detector array in a second orientation and a second position.

8. The method of claim 1, further comprising generating i) a first X-ray beam via an X-ray source of the gantry when capturing the first image of the central region, and ii) a second X-ray beam via the X-ray source when capturing the first image of the annulus region, wherein:

the first X-ray beam overlaps the second X-ray beam; and image data associated with the overlap of the first X-ray beam and the second X-ray beam is reweighted to account for redundant sampling during back projection.

9. The method of claim 1, further comprising:

generating third projected and interpolated padding data for a second image of the central region based on a second image of the annulus region, the first set of images comprising the second image of the central region, and the second set of images comprising the second image of the annulus region;

generating a second extended image of the central region based on the third projected and interpolated padding data;

generating fourth projected and interpolated padding data for the second image of the annulus region based on the second image of the central region;

generating a second extended image of the annulus region based on the fourth projected and interpolated padding data; and performing back projection to reconstruct an image of the imaging volume based on the second extended image of the central region and the second extended image of the annulus region.

10. The method of claim 4, wherein the reorienting and repositioning of the X-ray source and the detector array comprises maintaining the X-ray source at a same radial distance from an isocenter of the gantry, tilting the X-ray source and the detector array, and repositioning the detector array relative to the X-ray source to capture images of the annulus region.

11. The method of claim 5, further comprising, subsequent to ramp filtering, cropping the first extended image of the central region and the first extended image of the annulus region, wherein the back projection is performed subsequent to the cropping of the first extended image of the central region and the first extended image of the annulus region.

12. An imaging system comprising:

a gantry comprising an aperture having an imaging volume in which a subject is disposed, the gantry comprising an X-ray source and a detector array arranged to rotate about an isocenter of the gantry; and at least one processor configured to:

spin the gantry a first time to capture via the detector array a first set of images of a central region of the imaging volume;

spin the gantry a second time to capture via the detector array a second set of images of an annulus region of the imaging volume surrounding the central region;

generate first projected and interpolated padding data for a first image of the central region by projecting and interpolating image data on a second detector plane associated with the detector array being in a second orientation and second position for capturing the second set of images to an extended portion of a first detector plane associated with the detector array being in a first orientation and first position for capturing the first set of images, the first set of images comprising the first image of the central region, and the second set of images comprising the first image of the annulus region;

generate a first extended image of the central region based on the first projected and interpolated padding data;

generate second projected and interpolated padding data for the first image of the annulus region by projecting and interpolating image data on the first detector plane to an extended portion of the second detector plane;

generate a first extended image of the annulus region based on the second projected and interpolated padding data; and perform back projection to reconstruct an extended field-of-view image of the imaging volume based on the first extended image of the central region and the first extended image of the annulus region.

13. The imaging system of claim 12, wherein the central region of the imaging volume is centered on the isocenter.

14. The imaging system of claim 12, wherein:

the central region of the imaging volume is not centered on the isocenter of the gantry; and the isocenter is included in each of the first set of images.

15. The imaging system of claim 12, wherein the at least one processor is further configured to:

orient and position the X-ray source and the detector array to capture the first set of images; and reorient and reposition the X-ray source and the detector array to capture the second set of images.

16. The imaging system of claim 12, wherein the at least one processor is further configured to:

generate the second projected and interpolated padding data including a geometric projection onto the extended portion of the first detector plane, the first detector plane corresponding to a detection surface of the detector array in the first orientation and the first position; and generate the first projected and interpolated padding data including a geometric projection onto the extended portion of the second detector plane, the second detector plane corresponding to the detection surface of the detector array in the second orientation and the second position.

17. The imaging system of claim 12, wherein:

the X-ray source is configured to generate a first X-ray beam when capturing the first image of the central region and a second X-ray beam when capturing the first image of the annulus region;

the first X-ray beam overlaps the second X-ray beam; and image data associated with the overlap of the first X-ray beam and the second X-ray beam is reweighted to account for redundant sampling during back projection.

18. The imaging system of claim 12, wherein the at least one processor is further configured to:

generate third projected and interpolated padding data for a second image of the central region based on a second image of the annulus region, the first set of images comprising the second image of the central region, and the second set of images comprising the second image of the annulus region;

generate a second extended image of the central region based on the third projected and interpolated padding data;

generate fourth projected and interpolated padding data for the second image of the annulus region based on the second image of the central region;

generate a second extended image of the annulus region based on the fourth projected and interpolated padding data; and perform back projection to reconstruct an image of the imaging volume based on the second extended image of the central region and the second extended image of the annulus region.

19. The imaging system of claim 15, wherein the at least one processor is further configured to, while reorienting and repositioning the X-ray source and the detector array, maintain the X-ray source at a same radial distance from the isocenter, tilt the X-ray source and the detector array, and reposition the detector array relative to the X-ray source to capture images of the annulus region.

20. The imaging system of claim 12, wherein the at least one processor is further configured to:

pad the first extended image of the central region based on edge pixel data of the first extended image of the central region; and pad the first extended image of the annulus region based on edge pixel data of the first extended image of the annulus region.

21. The imaging system of claim 20, wherein the at least one processor is further configured to, subsequent to padding, ramp filter the first extended image of the central region and the first extended image of the annulus region.

22. The imaging system of claim 21, wherein the at least one processor is further configured to:

subsequent to ramp filtering, crop the first extended image of the central region and the first extended image of the annulus region; and perform the back projection subsequent to cropping the first extended image of the central region and the first extended image of the annulus region.

* * * * *